United States Patent
Shah

(10) Patent No.: US 6,712,832 B2
(45) Date of Patent: Mar. 30, 2004

(54) LOW-PRESSURE MEDICAL BALLOONS AND METHOD OF MAKING SAME

(76) Inventor: Tilak M. Shah, 104 Lochberry La., Cary, NC (US) 27511

( * ) Notice: Subject to any disclaimer, the term of this patent is extended or adjusted under 35 U.S.C. 154(b) by 220 days.

(21) Appl. No.: 09/977,644

(22) Filed: Oct. 15, 2001

(65) Prior Publication Data

US 2003/0074017 A1 Apr. 17, 2003

(51) Int. Cl.[7] .............................................. A61M 29/00
(52) U.S. Cl. ........................................ 606/192; 604/103
(58) Field of Search ................................ 606/190, 191, 606/192, 197, 198, 199, 194; 604/96.01, 97.01, 101.01, 101.04, 103

(56) References Cited

U.S. PATENT DOCUMENTS

| | | | |
|---|---|---|---|
| 4,003,382 A | 1/1977 | Dyke | |
| 4,134,942 A | 1/1979 | Mirr et al. | |
| 4,284,396 A | 8/1981 | Thissen et al. | |
| 4,423,000 A | 12/1983 | Teraoka | |
| 4,661,095 A | * 4/1987 | Taller et al. | 606/192 |
| 4,913,701 A | 4/1990 | Tower | |
| 4,935,190 A | 6/1990 | Tennerstedt | |
| 5,352,199 A | 10/1994 | Tower | |
| 5,366,685 A | 11/1994 | Fujii et al. | |
| 5,447,497 A | 9/1995 | Sogard et al. | |
| 5,718,861 A | 2/1998 | Andrews et al. | |
| 6,086,556 A | * 7/2000 | Hamilton et al. | 606/192 |
| 6,221,042 B1 | 4/2001 | Adams | |
| 6,290,485 B1 | 9/2001 | Wang | |

* cited by examiner

*Primary Examiner*—Kevin T. Truong
(74) *Attorney, Agent, or Firm*—Steven J. Hultquist; Marianne Fuierer; Mimi Yang

(57) ABSTRACT

A low-pressure balloon, and method of forming same by the steps of: preheat a thin film of thermoplastic polymeric material to a sufficient temperature; forming two halves of the balloon on said thin film of thermoplastic polymeric material by vacuum suction; isolating the two halves of the balloon from said thin film of thermoplastic polymeric material; bonding the two halves together on their edges to form the low-pressure balloon by radio-frequency welding method; and inverting the low-pressure balloon from inside out to turn the rough bonded edge of the two halves into the interior side of the balloon.

18 Claims, 4 Drawing Sheets

LOW-PRESSURE MEDICAL BALLOONS AND METHOD OF MAKING SAME

BACKGROUND OF THE INVENTION

1. Field of the Invention

The present invention generally relates to low-pressure medical balloons and to a method for manufacturing low-pressure medical balloons. In a specific embodiment the invention relates to medical balloons made using thermo-vacuum and radio-frequency welding techniques.

2. Description of the Related Art

Low-pressure catheter balloons are important in procedures such as angioplasty and in the use of in-dwelling catheters, endotracheal tubes and other cardio-vascular, oncology, and urology devices wherein an inflatable cuff is required.

Natural rubber sheet and film, formed by coagulation of natural rubber latex (NRL), have long been widely used for production of such low-pressure catheter balloons. NRL is a highly elastic, very-low-durometer material exhibiting high tear resistance and high elongation. It has long been used to manufacture a wide range of healthcare products and components for medical devices.

However, there is an increasing proportion of the population of potential NRL users, particularly workers in the medical and related fields, as well as patients, who are unable to use latex products because of allergic reaction that occurs when such persons contact NRL products. Increasing reports are appearing in the medical literature of anaphylactic shock reactions attributed to exposure to latex products, as well as less serious but nonetheless irritating and painful instances of contact dermatitis. As a result of the frequency and severity of such problems, OSHA regulations and guidelines have been established requiring employers to provide workers exposed to blood-borne pathogens with adequate hypo-allergenic substitutes or effective alternatives, relative to use of natural rubber latex products.

Apart from problems associated with its antigenic character, NRL has limited tensile strength and tear resistance and is highly susceptible to cuts and punctures. Additionally, NRL has a limited shelf life, and is degradeable in character, becoming more fragile and brittle over time, particularly in elevated temperature environments, such as the tropical or sub-tropical climates.

Polyurethane and silicone polymers have properties desirable for many rubber goods heretofore made of natural latex rubber. Examples include thermoplastic elastomeric polyurethanes.

The dip molding technique employed for many NRL products can be employed with polyurethanes and silicones, but dip molding does not achieve all the advantages and benefits desired. For example, dip molding processes are expensive, because expensive solvents are typically required, which have associated environmental effects, including atmospheric pollution as well as fire and health concerns. Additionally, dip molding processes do not produce optimal film properties. It is difficult to continuously and reliably manufacture dip-molded films that are free of pin holes and porosity. It also is difficult to continuously and reliably achieve uniform film thicknesses that are required for many end uses of rubber films. Moreover, in application to the manufacture of medical catheter balloons, the balloons formed by dip molding techniques tend to have a relatively small body-to-neck ratio, usually substantially less than 5:1 for polyurethanes, and typically well below 7:1 for silicones. Such body-to-neck ratio limits the utility of the catheter balloon.

Extrusion blow molding is another conventional method for forming low-pressure catheter balloons. However, the mold for extrusion blow molding is usually expensive. Additionally, balloons produced by extrusion blow molding techniques invariably do not have uniform wall thickness, i.e., such balloons usually are too thin in the body portion and too thick in the neck portion, relative to the thickness characteristics desired.

Tubing blow molding is yet another widely used method for producing catheter balloons, but it is only suitable for manufacturing balloons having body diameters of less than 1 inch, due to the tubing effect. Additionally, the neck portion of the balloons generated by tubing blow molding techniques, like that by extrusion blow molding, is usually too thick.

Film welding methods when used to join two flat sheets of polymeric materials together to form a catheter balloon, also experience difficulties. Inflation of such catheter balloons is usually non-uniform, due to "pillowing" or so-called "pillow effect, in which the center of the balloon that is distant from the welded edges tends to stretch much thinner than the periphery of the balloon that is proximate to the welded edges with the result that the shape of the end portions of the balloon is conical and not the desired spherical or cylindrical shape.

The present invention contemplates a low-pressure catheter balloon article and a method for manufacturing low-pressure catheter balloons from thermoplastic polymeric materials such as polyurethane or silicone, which overcome the disadvantages of the techniques described hereinabove.

SUMMARY OF THE INVENTION

The present invention relates to balloons of a type used in medical procedures, and to a method of making such balloons.

The present invention in one aspect relates to a new method for manufacturing a low-pressure medical balloon used in connection with a catheter, including the steps of:

providing a thin film of thermoplastic polymeric material;

heating the thermoplastic polymeric thin film to a sufficient temperature for vacuum forming thereof;

forming a first half section for a balloon on the thermoplastic polymeric thin film by vacuum suction;

forming a second half section for the balloon on a same or different thermoplastic polymeric thin film by vacuum suction; and bonding the first half-section to the second half-section along edges of the half-sections to form the balloon.

Such method advantageously uses thermo-vacuum molding techniques for shaping the thin film thermoplastic polymeric material to form the half-sections for the balloon.

The invention relates in another aspect to a low pressure balloon article, of a spherical and non-pillowed character, formed of corresponding (e.g., symmetrical) panels of a thermoplastic polymeric film, bonded together at their margins, such as by ultrasonic welding or other suitable technique.

The thermoplastic polymeric materials employed in the practice of the present invention for the production of the balloon articles may be of any suitable type. Illustrative materials include polyurethanes and silicones, which do not induce allergic reactions. Polyurethane elastomer is a particularly preferred material of construction for manufacturing the balloons of the present invention.

As used herein, the phrase "sufficient temperature" or "sufficient temperature for vacuum forming" means a temperature above the softening temperature of the thermoplastic polymeric material. Such temperature is preferably above the Vicat softening temperature of the thermoplastic polymeric material, but below the deformation temperature of such thermoplastic polymeric material. The Vicat softening temperature of polyurethane elastomers, for example, is usually from about 60° C. to about 150° C., depending on the nature of the polymer. Such Vicat softening temperature is readily determinable within the skill of the art, without undue experimentation. By keeping the temperature below the deformation temperature, the thermoplastic polymeric film will not stick to the surfaces of the process devices that hold it for further processing.

At least one vacuum suction mold is provided for forming the first and second half sections of the catheter balloons. Such vacuum suction mold comprises at least one mold cavity of any desired shape, for example, semi-sphere, semi-cubic, semi-ellipsoid, and semi-hexagon. Such vacuum suction mold also comprises a plurality of vacuum suction holes that are connected to a vacuum pump. During the vacuum suction molding step, the heated and softened thermoplastic polymeric thin film is placed in proximity to the mold cavity of the vacuum suction mold, and the vacuum pump applies a negative pressure to the vacuum suction holes in the mold cavity. Such negative pressure functions to suck the thermoplastic polymeric thin film closely to the surface of the mold cavity of the vacuum suction mold and thereby conforms the thermoplastic polymeric film to the shape of the mold cavity. The polymeric thin film is vacuum-molded in such manner to yield a polymeric thin film article of a shape corresponding to that of the mold cavity.

The first and second half-sections of the balloon can be formed sequentially, or they can be formed simultaneously, on the same thin film of thermoplastic polymeric material, or on different sheets of thermoplastic polymeric material.

In a preferred embodiment of the present invention, the vacuum suction mold comprises a plurality of mold cavities, so that a single large thermoplastic elastic polymeric thin film can be readily molded into a plurality of halves at once, thereby enabling high-rate production which is particularly suitable for commercial manufacture of low-pressure medical balloons.

After thermo-vacuum molding, the first and second half-sections of the catheter balloon are recovered from the polymeric thin film(s) on which they have been formed, and before or after such recovery, are bonded together at their margins (edges) by any of various suitable bonding methods. Recovery of the half-sections from the thin film(s) on which they have been formed, can be carried out in any suitable manner, as for example by die cutting, severing of half-sections by a heated platen, laser cutting, etc. Illustrative of suitable bonding methods which may be employed in the broad practice of the invention are the following, which include, but are not limited to: adhesive bonding, electromagnetic bonding, hot plate welding, impulse heating, induction bonding, insert bonding, radio-frequency welding, spin welding, thermostacking, ultrasonic sealing, and vibration welding.

In one preferred embodiment of the present invention, the two half-sections of the catheter balloon are bonded together by radio-frequency welding as described in U.S. Pat. No. 5,833,915 for "Method of Welding Polyurethane Thin Film," issued on Nov. 10, 1998 to Tilak M. Shah, the contents of which hereby are incorporated herein by reference in their entirety, for all purposes of the present invention.

More specifically, the first and second half-sections of the balloon in one embodiment are bonded together according to the following sequence of steps:

heating a welding platen to a temperature above a Vicat softening temperature and below a melting temperature of the thermoplastic polymeric material;

placing edges of the first and second half-sections of the balloon on the preheated platen, so that the edges of the first and second half-sections of the balloon are heated by the platen to a temperature above the Vicat softening temperature and below the melting temperature of the thermoplastic polymeric material;

compressing the edges of the first and second half-sections of the balloon in opposing edge surface relationship to one another to form an interface therebetween, e.g., with opposedly facing mated edge surfaces of the respective half-sections being held under pressure between a die and welding platen;

transmitting radio-frequency energy to the opposedly facing mated edge surfaces of the respective half-sections being held under pressure, to bond the edge surfaces at the interface therebetween forming a weld; and cooling the weld, thereby yielding the balloon.

The catheter balloon formed by method of the present invention is characterized by uniform thickness throughout the body portion and/or neck portion of such balloon. The thermo-vacuum molding process conducted while the thermoplastic elastomeric film is at or above its softening temperature subjects the thermoplastic polymeric thin film to a minimum amount of distortion incident to stretching or expansion, and thus avoids fluctuations in wall thickness that otherwise result from uneven stretching or expansion in different regions of the film.

Moreover, because the thermo-vacuum molding is capable of molding the thermoplastic polymeric thin film into any desired shape, it is readily feasible to form balloons with a deep-drawn concave shape having a depth-to-width ratio $\leq 1:1$, of superior character and quality.

By way of specific example, the method of the present invention can be employed to form catheter balloons of a perfect spherical shape (see FIG. 2), which has not been possible using prior art techniques. Such perfect spherical catheter balloons many important application advantages: by placing the catheter in the center of a spherical balloon, concentric expansion of such balloon can be achieved; the distance from the central catheter to each and every point on such spherical balloon is the same, which means that uniformity of application of forces or therapeutic agents by such balloon can be achieved.

The welded edges of catheter balloons formed by the method of the present invention are usually rough, which may be undesirable in use of the balloons. Inverting such balloons places the rough welded edges on the interior of the balloons and therefore resolves issues associated with free edges of the seam on the exterior surface of the balloons.

DETAILED DESCRIPTION OF THE INVENTION, AND PREFERRED EMBODIMENTS THEREOF

Low-pressure catheter balloons are widely used in various medical applications, such as fixation of a catheter in a vessel or body cavity, occlusion of blood flow (sealing off a vessel during a procedure), radiation treatment, drug delivery, graft delivery, etc. Other applications for balloons of such type include brachytherapy, i.e., the treatment of malignant tumors with radioactive material, and heat therapy with elevated temperature solutions.

Low-pressure balloons are also used in a variety of cardio-vascular procedures. Applications include interaortic balloons, cardioplegia balloons (retrograde catheters), embolectomy/thrombolytic catheter balloons, intervascular and occlusion/transluminal catheters, catheters for minimally invasive bypass surgery, port-access catheters, and heart valve and thermodilation catheters. For ear, nose, and throat procedures, low-pressure balloon applications include tracheal-tube balloon and esophageal balloon catheters.

For radiation treatment and drug delivery purposes, it is especially important that the low-pressure balloons have uniform wall thickness and concentric expansion during their inflation, so that the amount of radiation or drug applied to the surrounding tissues around the balloon can be correspondingly uniform, able to be well-standardized and quantified.

As described hereinabove, it has not been possible to provide high quality medical balloons of uniform wall thickness. Moreover, the shapes of the medical balloons that can be formed by the methods of the prior art are very limited, usually characterized by a substantial "neck" portion whose diameter is less than 1 inch. Such neck portion usually undergoes less expansion than the remaining "body" portion of the balloon, and frequently is too thick for radiation treatment or drug delivery purposes. Medical balloons produced by techniques of the prior art typically have a neck to body ratio of more than 30%.

The present invention provides a method for manufacturing high quality medical balloons, which are characterized by a uniform wall thickness, which may for example be in a range of from about 0.5 mils to about 10 mils (0.0127 mm to 0.254 mm), more preferably within a range of from about 2 mils to about 6 mils (0.0508 mm to 0.1524 mm). The neck to body ratio of balloons formed in accordance with the present invention may be less than 30%, preferably less than 25%, and more preferably less than 10%. Such high quality medical balloon also may be formed with a shape characterized by a depth-to-width ratio greater than 1:2, and more preferably in the vicinity of 1:1.

Figure 1:
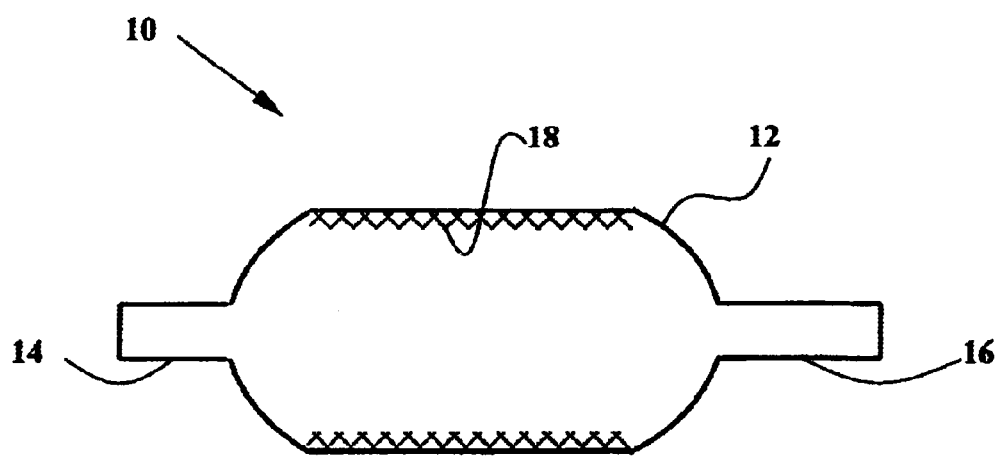
FIGS. 1 and 2 show longitudinal cross-sectional views of catheter balloons according to two embodiments of the present invention.

FIG. 1 shows the longitudinal cross-sectional view of a low-pressure catheter balloon 10 according to one embodiment of the present invention. Such balloon comprises an inflatable portion 12 and two collars 14 and 16 for mounting the balloon 10 onto a catheter (not shown). Welded edge 18 that joins the two halves of the balloon 10 (see FIGS. 4 and 5) has been inverted into the interior volume of the balloon 10, so that such welded edge 18 does not extend outwardly and irritate or damage surrounding tissues when the balloon 10 is inserted into a blood vessel or a body organ.

Figure 2:
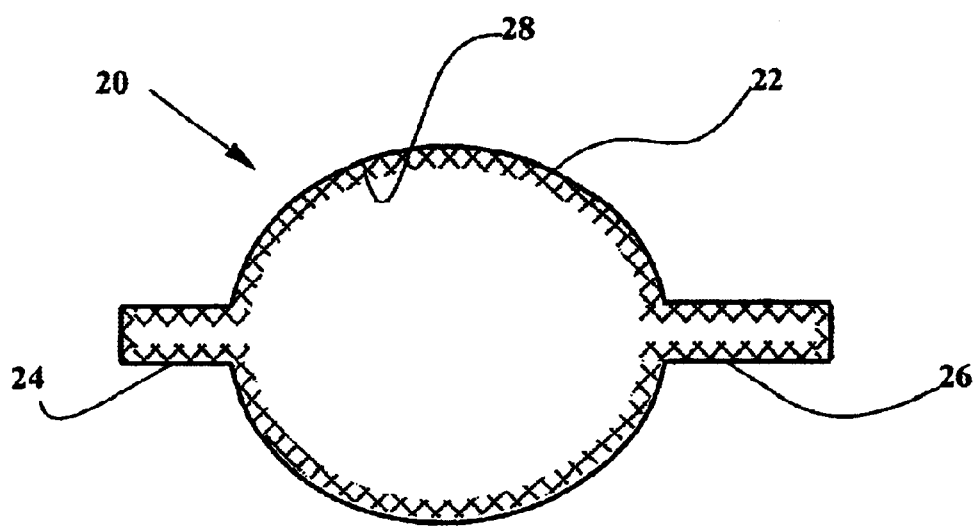

FIG. 2 shows a longitudinal cross-sectional view of another low-pressure catheter balloon 20 having an inflatable portion 22, two collars 24 and 26, and an inverted welded edge 28. The balloon 20 has a perfect spherical shape, so that a drug or radiation source (radiation seed or isotopic particle; not shown) can be placed in the center of the balloon 20 for uniform drug delivery or radiation treatment.

Figure 3A:
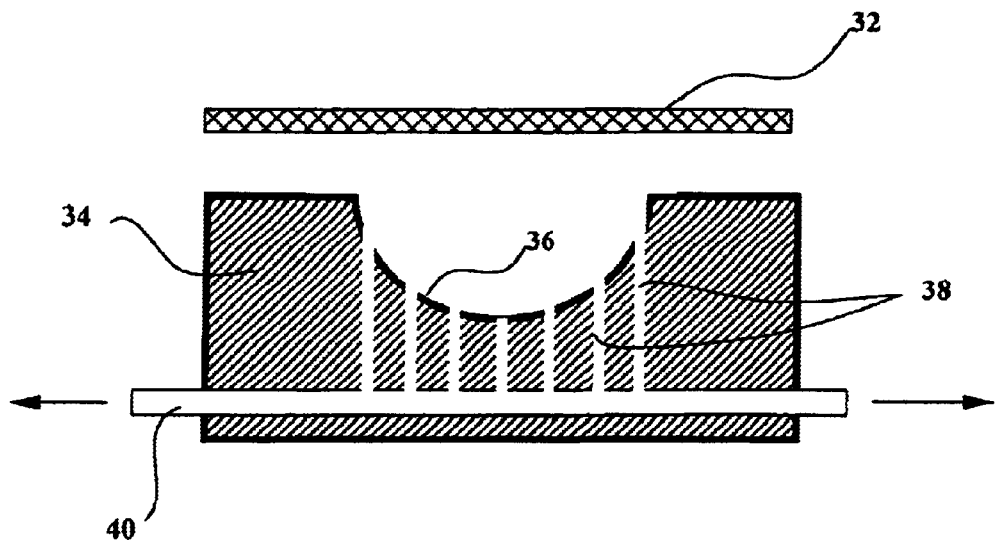
FIGS. 3A and 3B show an illustrative thermo-vacuum molding process for forming a half-section of a catheter balloon of a general type shown in FIG. 2.
Figure 3B:
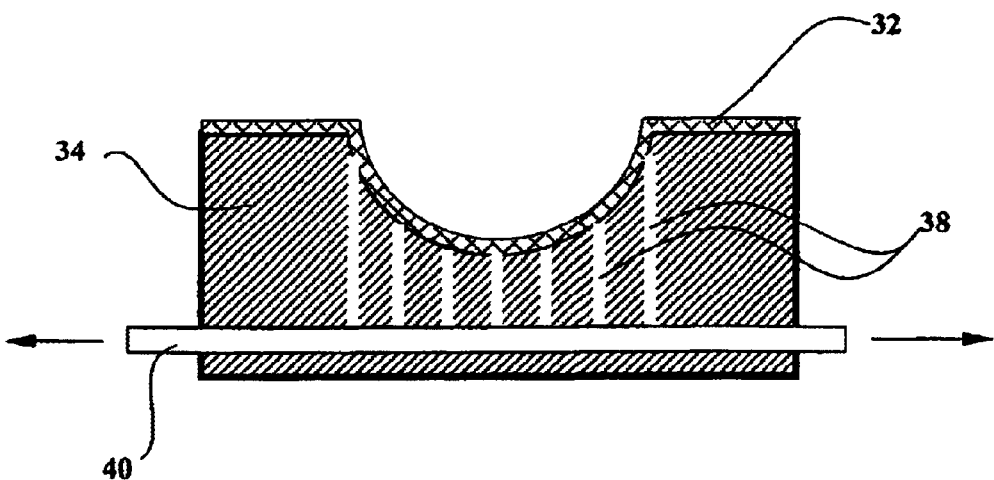

FIG. 3A shows a thermoplastic elastomeric polymer thin film 32, which has been heated to a softened condition. Such thermoplastic polymeric thin film 32 is placed immediately above a vacuum suction mold 34. The vacuum suction mold 34 comprises a concave mold cavity 36 of any desired size and dimensions. Although FIG. 3A illustrates a semi-spherical mold cavity 36, such illustration is a simplified example and should not be construed as limiting the broad scope of the present invention. The vacuum suction mold 34 also comprises a plurality of vacuum suction holes 38 on the mold cavity 36, which holes are connected to a suction manifold 40. A negative pressure can be applied between the surface of the mold cavity 36 and the thermoplastic thin film 32, by drawing air from the suction manifold 40 and the vacuum suction holes 38, using a vacuum pump (not shown) or any other suitable devices (extractor, eductor, cryopump, etc.). Such negative pressure functions to suck the thermoplastic polymeric thin film 32 into the mold cavity, as shown in FIG. 3B, and conforms the thermoplastic thin film 32 to the shape of the mold cavity.

In order to prevent the thermoplastic polymeric thin film 32 from sticking to the mold 34 after completion of the molding process, it is desirable to use polymeric materials characterized by a low coefficient of friction (COF), usually less than 2, preferably less than 1, more preferably less than 0.5, and most preferably less than 0.15.

Figure 4:
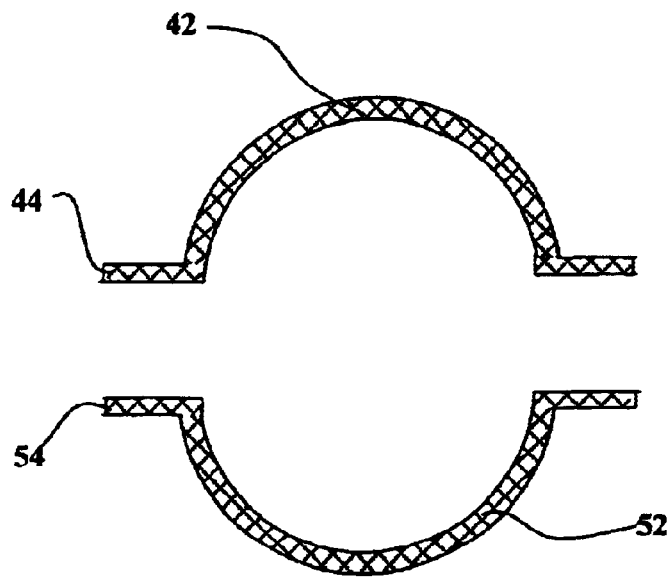
FIGS. 4 and 5 illustrate the process of joining a first and second half-sections of a catheter balloon to form the product balloon article.

After molding of a first half section 42 and a second half section 52, as shown in FIG. 4, the two half sections 42 and 52 may be separated from the rest of the thermoplastic film, with each half comprising an edge, shown as 44 and 54. The first half section 42 can be bonded to the second half section 52 at the edges 44 and 54 to form a single balloon 60, as illustrated in FIG. 5, with the bonded edges 44 and 54 thereby fused into a bonding trim 62.

Figure 5:
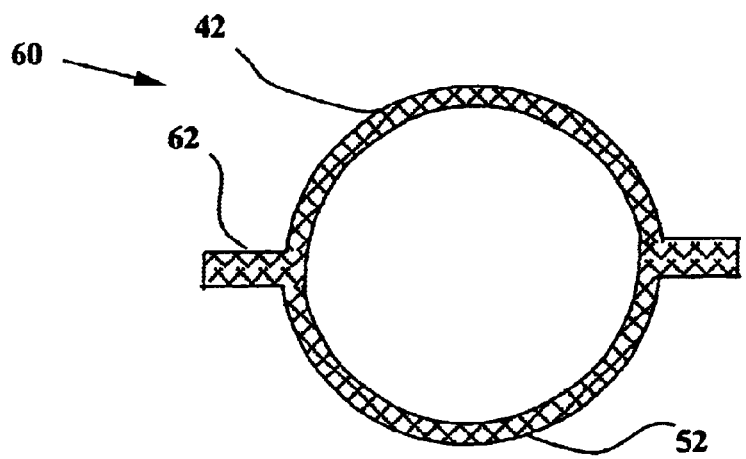
Figure 6:
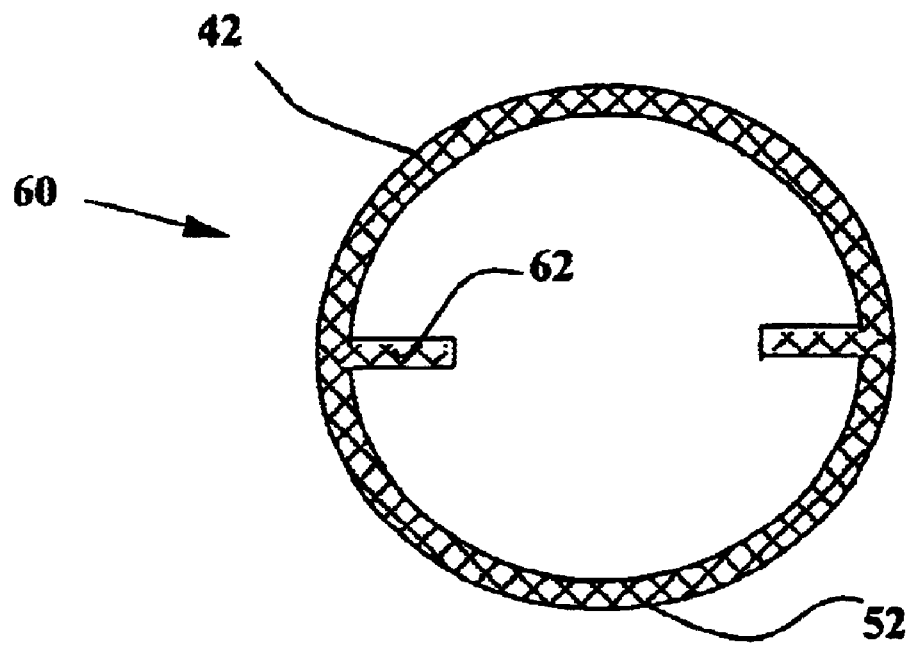
FIG. 6 shows a transverse cross-sectional view of the catheter balloon of FIG. 5 after inversion.

FIG. 6 shows the balloon 60 formed as in FIG. 5, which has been inverted from inside out, so that the bonding trim 62 is turned to the interior of the balloon 60, thereby forming a smooth exterior surface for balloon 60.

While the invention has been described herein with respect to various illustrative aspects, features and embodiments, it will be recognized that the invention is not thus limited, but that the present invention extends to and encompasses other features, modifications, and alternative embodiments, as will readily suggest themselves to those of ordinary skill in the art based on the disclosure and illustrative teachings herein. The claims that follow are therefore to be construed and interpreted as including all such features, modifications and alternative embodiments, within their spirit and scope.

What is claimed is:

1. A method for manufacturing low-pressure balloon, comprising the steps of:
   (a) providing a thin film of thermoplastic polymeric material;
   (b) heating the thermoplastic polymeric thin film to a sufficient temperature for vacuum forming thereof;
   (c) forming a first half section for a balloon on the thermoplastic polymeric thin film by vacuum suction;

(d) forming a second half section for the balloon on a same or different thermoplastic polymeric thin film by vacuum suction; and (e) bonding the first half-section to the second half-section along edges of the half-sections to form the balloon.

2. A method according to claim 1, wherein the thermoplastic polymeric material is non-allergenic.

3. A method according to claim 1, wherein the thermoplastic polymeric material comprises a material selected from the group consisting of polyurethane and silicone.

4. A method according to claim 1, wherein the thermoplastic polymeric material comprises polyurethane.

5. A method according to claim 1, wherein the thin film of thermoplastic polymeric material is heated to a temperature within a range from about 60° C. to about 150° C.

6. A method according to claim 1, wherein the first and second half sections of the balloon are formed simultaneously on a same thin film of thermoplastic polymeric material by vacuum suction.

7. A method according to claim 1, wherein the first and second half sections of the balloon have uniform wall thickness.

8. A method according to claim 1, wherein the first and second half sections of the balloon have a shape selected from the group consisting of semi-sphere, semi-cubic, semi-ellipsoid, and semi-hexagon.

9. A method according to claim 1, wherein the first and second half sections of the balloon are semispherical.

10. A method according to claim 1, wherein the first and second half sections of the balloon are bonded together by a bonding method selected from the group consisting of: adhesive bonding, electromagnetic bonding, hot plate welding, impulse heating, induction bonding, insert bonding, radio-frequency welding, spin welding, thermostacking, ultrasonic sealing, and vibration welding.

11. A method according to claim 1, wherein the first and second half sections of the balloon are bonded together by radio-frequency welding.

12. A method according to claim 1, wherein the first and second halves of the balloon are bonded together by radio-frequency welding, comprising the steps of:

(a) preheating a welding platen to a temperature above a Vicat softening temperature and below a melting temperature of the thermoplastic polymeric material;

(b) placing edges of the first and second half sections of the balloon on the preheated platen, said platen heating the edges of the first and second halves of the balloon to a temperature above the Vicat softening temperature and below a melting temperature of said thermoplastic polymeric material;

(c) compressing the edges of the first and second halves of the balloon at edges thereof to form an interface therebetween;

(d) transmitting radio-frequency energy to the edges of the first and second half sections of the balloon while said edges are under pressure, and welding said edges at said interface, thereby forming a weld, and (e) recovering said balloon comprising the welded first and second half sections.

13. A method according to claim 1, further comprising the step of inverting the low-pressure balloon to dispose rough bonded edges of said first and second half sections of the balloon on an interior surface of said balloon.

14. A method according to claim 1, wherein the low-pressure balloon has a wall thickness within a range from about 0.5 mils to about 10 mils.

15. A method according to claim 1, wherein the low-pressure balloon has a wall thickness within a range from about 2 mils to about 6 mils.

16. A method according to claim 1, wherein the low-pressure balloon has a neck to body ratio of less than 30%.

17. A method according to claim 1, wherein the low-pressure balloon has a neck to body ratio of less than 25%.

18. A method according to claim 1, wherein the low-pressure balloon has a neck to body ratio of less than 10%.

* * * * *

UNITED STATES PATENT AND TRADEMARK OFFICE
CERTIFICATE OF CORRECTION

PATENT NO.    : 6,712,832 B2
DATED         : March 30, 2004
INVENTOR(S)   : Shah, Tilak M.

It is certified that error appears in the above-identified patent and that said Letters Patent is hereby corrected as shown below:

Column 1,
Line 14, after "important in" insert -- various cardiology --;
Line 15, "procedures such as angioplasty" should be -- procedures --;

Column 2,
Line 33, "polyurethane or silicone," should be -- polyurethane --;
Line 61, "ultrasonic welding" should be -- ultrasonic welding, RF welding, --;
Line 66, "silicones" should be -- polyamide elastomers -; and Column 4,
Line 35, "avoids" should be -- minimizes --.

Signed and Sealed this

Twentieth Day of July, 2004

JON W. DUDAS
*Acting Director of the United States Patent and Trademark Office*